United States Patent [19]
Dvorak et al.

[11] Patent Number: 6,040,446
[45] Date of Patent: Mar. 21, 2000

[54] PROCESS FOR PREPARING A 2-(2-AMINO-1, 6-DIHYDRO-6-OXO-PURIN-9-YL) METHOXY-1,3-PROPANEDIOL DERIVATIVE

[75] Inventors: Charles A. Dvorak; Douglas L. Wren, both of Palo Alto; Lawrence E. Fisher, Mountain View; Steven D. Axt, San Jose; Eric R. Humphreys, San Bruno; Humberto B. Arzeno, Cupertino; Colin C. Beard, Palo Alto, all of Calif.; Sam Linh Nguyen, Denver, Colo.; Yeun-Kwei Han, Louisville, Colo.; Christopher R. Roberts, Berthoud, Colo.; Jan P. Lund, Boulder, Colo.; Paul R. Fatheree, San Francisco, Calif.

[73] Assignee: Syntex (U.S.A.) Inc., Palo Alto, Calif.

[21] Appl. No.: 09/127,380

[22] Filed: Jul. 31, 1998

Related U.S. Application Data

[63] Continuation-in-part of application No. 08/779,540, Jan. 8, 1997, abandoned, which is a continuation-in-part of application No. 08/592,079, Jan. 26, 1996, abandoned.

[51] Int. Cl.$^7$ .................................................. C07D 473/18
[52] U.S. Cl. ........................... 544/276; 560/106; 560/254
[58] Field of Search ............................................... 544/276

[56] References Cited

U.S. PATENT DOCUMENTS

| | | | |
|---|---|---|---|
| 4,355,032 | 10/1982 | Verheyden et al. | 424/253 |
| 5,043,339 | 8/1991 | Beauchamp | 514/274 |
| 5,856,481 | 1/1991 | Nestor | 544/276 |

FOREIGN PATENT DOCUMENTS

| | | |
|---|---|---|
| 0 308 065 | 3/1985 | European Pat. Off. . |
| 0 158 847 | 10/1985 | European Pat. Off. . |
| 0 375 329 | 6/1990 | European Pat. Off. . |
| 0 532 878 | 3/1993 | European Pat. Off. . |
| 1 523 865 | 6/1978 | United Kingdom . |
| 2 104 070 | 3/1983 | United Kingdom . |
| 2 122 618 | 1/1984 | United Kingdom . |
| 8829571 | 6/1990 | United Kingdom . |
| WO 94/29311 | 12/1994 | WIPO . |

OTHER PUBLICATIONS

E. Jensen et al., *Acta Pharm. Nord.* 3(4) 243–247 (1991).
John C. Martin et al., *J. Pharm. Sci.* 76(2), p. 180–184 (1987).
P.C. Maudgal et al., *Arch. Ophthalmol.* 1984; 102: 140–142.
Leon Colla et al.,*J. Med. Chem.* 98, 3, 26, 602–604 (1983).
L. M. Beauchamp et al., *Antiviral Chemistry & Chemotherapy* (1992), 3 (3), 157–164.

*Primary Examiner*—Mark L. Berch
*Attorney, Agent, or Firm*—Heller Ehrman White & McAuliffe LLP

[57] ABSTRACT

Process and novel intermediates for preparing the L-monovaline ester of 2-(2-amino-1,6-dihydro-6-oxo-purin-9-yl) methoxy-1,3-propanediol and its pharmaceutically acceptable salts. The present process and intermediates provide for reduced impurities in the mono-valine ester end-product and lower overall production costs. The process involves the condensation of a silylated guanine compound with a substituted glycerol derivative and esterification of this product with an L-valine derivative. These mono-valine products are of value as antiviral agents with improved absorption.

17 Claims, No Drawings

PROCESS FOR PREPARING A 2-(2-AMINO-1, 6-DIHYDRO-6-OXO-PURIN-9-YL) METHOXY-1,3-PROPANEDIOL DERIVATIVE

CROSS-REFERENCE TO RELATED APPLICATIONS

This application is a continuation-in-part of application Ser. No. 08/779,540, filed Jan. 8, 1997, abandoned, which is in turn a continuation-in-part of application Ser. No. 08/592,079, filed Jan. 26, 1996, now abandoned.

BACKGROUND OF THE INVENTION

1. Field of the Invention

The present invention relates to a process for preparing a prodrug formulation of ganciclovir and its pharmaceutically acceptable salts. More specifically, the invention relates to a process for preparing the L-monovaline ester derived from 2-(2-amino-1,6-dihydro-6-oxo-purin-9-yl)methoxy-1,3-propanediol and its pharmaceutically acceptable salts. The invention also relates to novel intermediates useful in the above process and to a process for preparing the intermediates.

2. Background Information

British Patent 1 523 865 describes antiviral purine derivatives with an acyclic chain in the 9-position. Among those derivatives 2-(2-amino-1,6-dihydro-6-oxo-purin- 9-yl) methoxy-ethanol with the INN name acyclovir has been found to have good activity against herpes viruses such as herpes simplex.

U.S. Pat. No. 4,355,032 discloses the compound 9-[(2-hydroxy-1-hydroxymethylethoxy)methyl]guanine or 2-(2-amino-1,6-dihydro-6-oxo-purin-9-yl)methoxy-1,3-propanediol with the INN name ganciclovir. Ganciclovir is highly efficacious against viruses of the herpes family, for example, against herpes simplex and cytomegalovirus.

British Patent Application GB 2 122 618 discloses derivatives of 9-(2-hydroxyethoxymethyl)guanine of the generic formula:

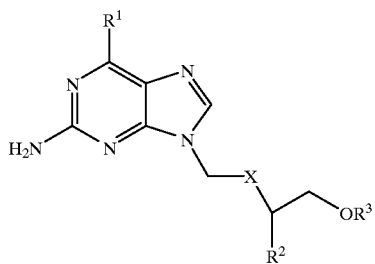

wherein X represents an oxygen or sulfur atom, $R^1$ represents a hydroxy or an amino group, $R_2$ represents a hydrogen atom or a group of the formula $CH_2OR^3{}_a$ and $R^3$ and $R^3{}_a$ may be the same or different, each represents an amino acid acyl radical and physiologically acceptable salts thereof. These compounds can be prepared by condensing a guanine derivative with a side chain intermediate in a strong polar solvent such as dimethylformamide or hexamethylphosphoramide, advantageously in the presence of a base, or by thermal condensation in the presence of a strong acid. These compounds are useful for the treatment of viral infections and have high water solubility which renders them of value in the formulation of aqueous pharmaceutical preparations. While the generic formula in the British patent application includes compounds in which $R^2$ is the group $-CH_2OR^3{}_a$, specific compounds of this group are not disclosed.

European Patent Application 0 375 329 A2 discloses prodrug compounds with the following formula

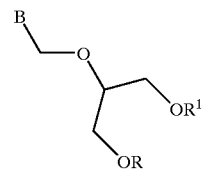

wherein R and $R^1$ are independently selected from hydrogen and an amino acid acyl residue providing at least one of R and $R^1$ represents an amino acid acyl residue and B represents a group of the formulae

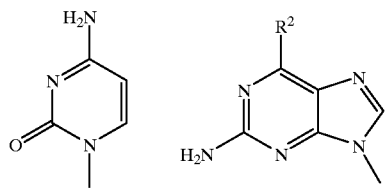

in which $R^2$ represents a $C_{1-6}$ straight chain, $C_{3-6}$ branched chain or $C_{3-6}$ cyclic alkoxy group, or a hydroxy or amino group or a hydrogen atom and the physiologically acceptable salts thereof. These prodrug compounds are described as having advantageous bioavailability when administered by the oral route, resulting in high levels of the parent compound in the body.

Example 3(b) of European Patent Application 0 375 329 discloses the preparation of the bis(L-isoleucinate) ester of ganciclovir as a white foam. Example 4(b) discloses the preparation of the bis(glycinate) ester of ganciclovir as a white solid. Example 5(b) discloses the preparation of the bis(L-valinate) ester of ganciclovir as a solid. Example 6(b) discloses the preparation of the bis(L-alaninate) ester of ganciclovir as a syrup containing 90% of the bis-ester and 10% of the monoester. The bis-esters are prepared by reacting ganciclovir with an optionally protected amino acid or functional equivalent thereof; the reaction may be carried out in a conventional manner, for example in a solvent such as pyridine, dimethylformamide, etc., in the presence of a coupling agent such as 1,3-dicyclohexylcarbodiimide, optionally in the presence of a catalytic base such as 4-dimethylaminopyridine. The described bis-esters are non-crystalline materials which are difficult to process for the manufacture of oral pharmaceutical dosage forms.

British Patent Application No. 8829571 is the priority patent application for European Patent Application 0 375 329 and U.S. Pat. No. 5,043,339, and discloses amino acid esters of the compounds of the formula

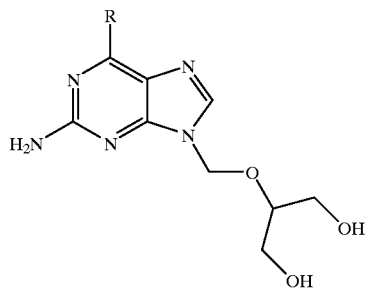

wherein R represents a hydroxy or amino group or a hydrogen atom) and the physiologically acceptable salts thereof. Examples of preferred amino acids include aliphatic acids, e.g., containing up to 6 carbon atoms such as glycine, alanine, valine and isoleucine. The amino acid esters include both mono and diesters. The preparation of the diesters is identical to the preparation in European Patent Application 0 375 329; however, this patent application as well as European Patent Application 0 375 329 and U.S. Pat. No. 5,043,339 do not disclose the preparation of monoesters, or any data suggesting their usefulness.

Leon Colla et al., J. Med. Chem. (1983) 26, 602–604 disclose several water-soluble ester derivatives of acyclovir and their salts as prodrugs of acyclovir. The authors indicate that acyclovir cannot be given as eye drops or intramuscular injections because of its limited solubility in water and have therefore synthesized derivatives of acyclovir which are more water soluble than the parent compound. The authors disclose the hydrochloride salt of the glycyl ester, the hydrochloride salt of the alanyl ester, the hydrochloride salt of the beta-alanyl ester, the sodium salt of the succinyl ester, and the azidoacetate ester. The alanyl esters were prepared by conventional esterification methods, including reacting acyclovir with the corresponding N-carboxy-protected amino acid in pyridine, in the presence of 1,3-dicyclohexylcarbodiimide and a catalytic amount of p-toluenesulfonic acid and subsequent catalytic hydrogenation to give the alpha- and beta-alanyl esters as their hydrochloride salts.

L. M. Beauchamp et al., Antiviral Chemistry & Chemotherapy (1992), 3(3), 157–164 disclose eighteen amino acid esters of the antiherpetic drug acyclovir and their efficiencies as prodrugs of acyclovir, evaluated in rats by measuring the urinary recovery of acyclovir. Ten prodrugs produced greater amounts of the parent drug in the urine than acyclovir itself: the glycyl, D,L-alanyl, L-alanyl, L-2-aminobutyrate, D,L-valyl, L-valyl, DL-isoleucyl, L-isoleucyl, L-methionyl, and L-prolyl ester. According to the authors the L-valyl ester of acyclovir was the best prodrug of the esters investigated. These esters were prepared by methods similar to those employed by Colla et al.

European Patent Application 0 308 065 A2 discloses the valine and isoleucine esters of acyclovir, preferably in the L-form, as showing a large increase in absorption from the gut after oral administration, when compared with other esters and acyclovir. The amino acid esters are prepared by conventional esterification methods, including reacting acyclovir with an N-carboxy-protected amino acid or an acid halide or acid anhydride of the amino acid, in a solvent such as pyridine or dimethylformamide, optionally in the presence of a catalytic base. The amino acid esters of acyclovir may also be prepared by condensing a guanine derivative with an amino acid side-chain intermediate in a manner analogous to that disclosed in British Patent Application GB 2 122 618, discussed above.

PCT Patent Application WO 94/29311 discloses a process for the preparation of amino acid esters of a nucleoside analogue, including acyclovir and ganciclovir. This process comprises reacting a nucleoside analogue having an esterifiable hydroxy group in its linear or cyclic ether moiety, with a 2-oxa-4-aza-cycloalkane-1,3-dione of the formula

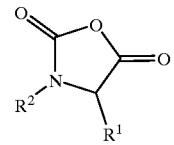

wherein $R^1$ may represent hydrogen, $C_{1-4}$ alkyl or alkenyl group or other amino acid side chains, and $R^2$ may represent hydrogen or a group $COOR^3$ where $R^3$ is a benzyl, t-butyl, fluorenylmethyl or an optionally halo substituted linear or branched $C_{1-8}$ alkyl group. Preferred $R^1$ groups include hydrogen, methyl, isopropyl and isobutyl, yielding respectively the glycine, alanine, valine and isoleucine esters of acyclovir or ganciclovir. Examples 1–3 of PCT Patent Application WO 94/29311 discloses only the condensation of acyclovir with the valine-substituted 2-oxa-4-aza-cycloalkane-1,3-dione (Z-valine-N-carboxyanhydride) by conventional procedures. While the amino acid esters of the PCT application include both the acyclovir and ganciclovir (DHPG) esters, the application does not disclose how to prepare the ganciclovir esters, much less the mono-esters of ganciclovir.

The L-monovaline ester derived from 2-(2-amino-1,6-dihydro-6-oxo-purin-9-yl)methoxy-1,3-propanediol and its pharmaceutically acceptable salts are potent antiviral agents and are described in European Patent Application 0 694 547 A. These compounds have been found to have improved oral absorption and low toxicity. This patent application also discloses certain processes for preparing these esters, different from those described herein.

The present invention relates to an improved process and novel intermediates whereby an acid addition salt of a mono-hydroxy protected ganciclovir is formed as a novel intermediate, which reduces impurities in the mono-valine ester end-product, compared to known intermediates. This also eliminates the costly and time consuming purification steps and allows the use of starting materials of lower purity, which, in turn, reduces overall production costs.

SUMMARY OF THE INVENTION

In a first aspect, this invention provides a process for preparing the compound of the formula (I):

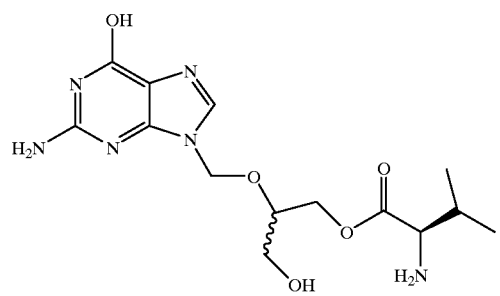

and pharmaceutically acceptable salts thereof, which compound is named hereinafter 2-(2-amino-1,6-dihydro- 6-oxo-purin-9-yl)methoxy-3-hydroxy-1-propyl-L-valinate or mono-L-valine ganciclovir.

This process involves the condensation of a silylated guanine compound with a substituted glycerol derivative, optionally followed by formation of an acid addition salt of a mono-hydroxy protected ganciclovir as an intermediate; esterification of this product with an L-valine derivative and the removal of any protecting groups forms the prodrug of Formula (I). Optionally, the process can also include the formation of salts of the prodrug of Formula (I), the conversion of an acid addition salt of the prodrug of Formula (I) into a non-salt form, the optical resolution of a prodrug of Formula (I) or the preparation of the prodrugs of Formula (I) in crystalline form. Details of the process are described below.

In a second aspect, this invention provides compounds of Formula (IV) and Formula (V) which are useful intermediates for preparing mono-L-valine ganciclovir and its pharmaceutically acceptable salts.

The compounds of Formula (IV) are:

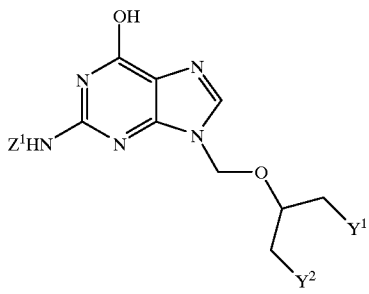

wherein $Z^1$ is hydrogen or an amino-protecting group, $Y^1$ is halo, lower acyloxy or aralkyloxy, and $Y^2$ is lower acyloxy.

The compounds of Formula (V are:

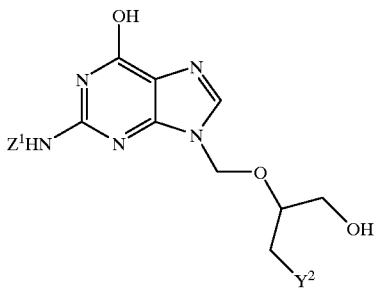

wherein $Z^1$ is hydrogen or an amino-protecting group, $Y^2$ is halo, lower acyloxy or aralkyloxy. Compounds of Formula (V) may optionally be converted into an acid addition salt; preferred is the hydrochloride salt.

A third aspect of this invention is a process for preparing the novel intermediates of Formula (IV) and (V).

DETAILED DESCRIPTION OF THE INVENTION

Definitions

Unless otherwise stated, the following terms used in the specification and claims have the meanings given below:

"BOC" means t-butoxycarbonyl.

"CBZ" means carbobenzyloxy (benzyloxycarbonyl).

"FMOC" means N-(9-fluorenylmethoxycarbonyl).

"DHPG" means 9-[(1,3-dihydroxy-2-propoxy)methyl] guanine.

"Alkyl" means a straight or branched saturated hydrocarbon radical having from 1–12 or one to the number of carbon atoms designated. For example, $C_{1-7}$ alkyl is alkyl having at least one but no more than seven carbon atoms, e.g. methyl, ethyl, i-propyl, n-propyl, n-butyl, n-pentyl, n-heptyl and the like.

"Lower alkyl" means an alkyl of one to six carbon atoms.

"Aryl" means an organic radical derived from an aromatic hydrocarbon by the removal of one hydrogen atom. Preferred aryl radicals are aromatic carbocyclic radicals having a single ring (e.g., phenyl) or two condensed rings (e.g. naphthyl).

"Aralkyl" means an alkyl group in which an alkyl hydrogen atom is replaced by an above-defined aryl group.

"Acyl" means an organic radical of the formula R—C (O)—, derived from an organic acid by the removal of the hydroxyl group; R is alkyl or aryl of 1–12 carbon atoms; e.g., $CH_3CO$— is the acyl radical of acetic acid ($CH_3COOH$), or acetyl. Another examples for acyl is propionyl. Benzoyl is the acyl radical of benzoic acid ($C_6H_6COOH$), etc.

"Lower acyl" refers to "acyl" when it represents "alkanoyl" which is the organic radical RCO— in which R is an alkyl group of 1–6 carbon atoms; preferred lower acyl groups are the acetyl and the propionyl radicals.

"Lower alkyloxy", "(lower alkyl)amino", "di(lower alkyl) amino", "(lower alkanoyl)amino", and similar terms mean alkoxy, alkylamino, dialkylamino, alkanoylamino, etc. in which the or each alkyl radical is a "lower alkyl" as described above.

"Halogen" or "halo" means fluorine, chlorine, bromine, or iodine.

"Trityl" means the triphenylmethyl radical $(PH)_3C$—.

"Mesyl" means the methanesulfonyl radical $CH_3SO_2$—.

"Tosyl" means the p-toluenesulfonyl radical $CH_3C_6H_5SO_2$—.

"Aprotic (nonpolar) solvent" means organic solvents such as diethyl ether, ligroin, pentane, hexane, cyclohexane, heptane, octane, benzene, toluene, dioxane, tetrahydrofuran, carbon tetrachloride, and the like.

"Phase transfer catalyst" means a catalyst which alters the rate of transfer of water-soluble reactant across the interface to the organic phase. Suitable catalysts are, e.g., tetrabutylammonium chloride, tetrabutylammonium bromide, tetrabutylphosphonium chloride, tetrabutylphosphonium bromide, and N-2-ethylhexyl-4-dimethylamino pyridinium bromide "Derivative" of a compound means a compound obtainable from the original compound by a simple chemical process.

"Activated derivative" of a compound means a reactive form of the original compound which renders the compound active in a desired chemical reaction, in which the original compound is only moderately reactive or non-reactive. Activation is achieved by formation of a derivative or a chemical grouping within the molecule with a higher free energy content than that of the original compound, which renders the activated form more susceptible to react with another reagent. In the context of the present invention activation of the carboxy group is of particular importance and corresponding activating agents or groupings which activate the carboxy group are described in more detail below. An example of an activated derivative of L-valine is the compound of Formula (VI):

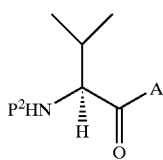

wherein $p^2$ is an amino-protecting group and A is a carboxy-activating group, for example, halo, a lower acyloxy group, a carbodiimide group such as 1-ethyl-3-(3-dimethylaminopropyl) carbodiimide (EDAC), an isobutyrate group, and the like.

Of particular interest for the present invention is an amino acid anhydride which is an activated form of an amino acid which renders the amino acid (especially L-valine) susceptible to esterification. Amino acid anhydrides are included in the compounds of Formula (VI), above. Especially useful for the present invention are the cyclic amino acid anhydrides of L-valine, described in PCT Patent Application WO 94/29311, such as 2-oxa-4-aza-5-isopropyl-cycloalkane-1,3-dione of Formula (VIa):

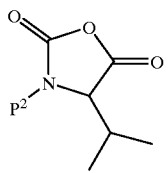

in which $p^2$ is an amino protecting group. Other examples of the cyclic amino acid anhydrides are protected amino acid N-carboxyanhydrides (NCA's) described in more detail below.

"Protecting group" means a chemical group that (a) preserves a reactive group from participating in an undesirable chemical reaction; and (b) can be easily removed after protection of the reactive group is no longer required. For example, the benzyl group is a protecting group for a primary hydroxyl function.

"Amino-protecting group" means a protecting group that preserves a reactive amino group that otherwise would be modified by certain chemical reactions. The definition includes the formyl group or lower alkanoyl groups with 2 to 4 carbon atoms, in particular the acetyl or propionyl group, the trityl or substituted trityl groups such as the monomethoxytrityl group, dimethoxytrityl groups such as the 4,4'-dimethoxytrityl, the trichloroacetyl group, the trifluoroacetyl group, the silyl group, the phthalyl group, and the N-(9-fluorenylmethoxycarbonyl) or "FMOC" group, the allyloxycarbonyl group, or other protecting groups derived from halocarbonates such as $(C_6-C_{12})$aryl lower alkyl carbonates (such as the N-benzyloxycarbonyl group derived from benzylchlorocarbonate), or derived from biphenylalkyl halocarbonates, or tertiary alkyl halocarbonates such as tertiary butylhalocarbonates, in particular tertiary butylchlorocarbonate, or di(lower)alkyldicarbonates, in particular di(t-butyl)dicarbonate, and the triphenylmethyl halides such as triphenylmethyl chloride, and trifluoroacetic anhydride.

"Hydroxy-protecting group" means a protecting group that preserves a hydroxy group that otherwise would be modified by certain chemical reactions. In the context of the present invention, the hydroxy-protecting group can be an ether- or ester-forming group that can be removed easily after completion of all other reaction steps, such as a lower acyl group (e.g., the acetyl or propionyl group), or an aralkyl group (e.g., the benzyl group, optionally substituted at the phenyl ring).

"Silylation catalyst" as used herein refers to catalysts that promote the silylation of guanine, for example ammonium sulfate, p-toluenesulfonic acid, trifluoromethane sulfonic acid, trimethylsilyltrifluoromethane sulfonate, bistrimethylsilyl sulfonate, sulfuric acid, potassium butylsulfonate, ammonium perchlorate, sodium perchlorate, sodium borofluoride or tin tetrachloride.

"Silylating agent" as used herein refers to a compound capable of silylating guanine. A preferred silylating agent is hexamethyldisilazane (which will give a compound of Formula (II)) in which $R^5$, $R^6$, and $R^7$ are all methyl). However, many other silylating agents are known in the art. For example, guanine may be reacted with a trialkylsilyl halide of formula $SiR^5R^6R^7X$, in which $R^5$, $R^6$, and $R^7$ are independently lower alkyl and X is chloro or bromo, such as trimethylsilyl chloride, tert-butyldimethylsilyl chloride, and the like, preferably in the presence of about 1–2 molar equivalents of a base.

The silylated/persilylated compound of Formula (II) is represented as follows:

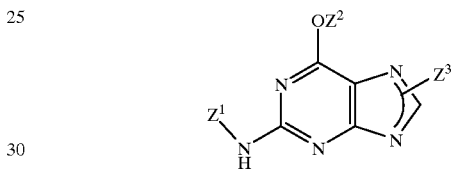

Formula (II) represents guanine protected by one, two, or three silyl groups, or a mixture thereof, where $Z^1$, $Z^2$, and $Z^3$ are independently hydrogen or a silyl group of formula $SiR^5R^6R^7$, provided that at least one of $Z^1$, $Z^2$, and $Z^3$ must be a silyl group, in which $R^5$, $R^6$, and $R^7$ are independently lower alkyl. It should be noted that Formula (II) as drawn represents a mixture of N-7 and N-9 isomers (as a tautomeric mixture).

Optionally, Formula (II) may represent the case where $Z^1$ is an amino-protecting group other than silyl as defined in the specification, and $Z^2$ and $Z^3$ are independently hydrogen or silyl.

"Leaving group" means a labile group that is replaced in a chemical reaction by another group. Examples of leaving groups are halogen, the-optionally substituted benzyloxy group, the mesyloxy group, the tosyloxy group or the acyloxy group.

All the activating and protecting agents employed in the preparation of the compound of Formula (I) must meet the following qualifications: (1) their introduction should proceed quantitatively and without racemization of the L-valine valine component; (2) the protecting group present during the desired reaction should be stable to the reaction conditions to be employed; and (3) the group must be readily removable under conditions in which the ester bond is stable and under which racemization of the L-valine component of the ester does not occur.

The process of the invention may also include the optical resolution of a prodrug of Formula (I). Terminology relating to the stereochemistry and optical resolution of these compounds is described in European Patent Application 0 694 547 A, incorporated herein by reference.

"Optional" or "optionally" means that a described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Pharmaceutically acceptable" means that which is useful in preparing a pharmaceutical composition that is generally safe and non-toxic and includes that which is acceptable for veterinary use as well as human pharmaceutical use.

"Pharmaceutically acceptable salts" means salts which possess the desired pharmacological activity and which are neither biologically nor otherwise undesirable. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentane-propionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene-1-carboxylic acid, glucoheptonic acid, 4,4'-methylene-bis(3-hydroxy-2-naphthoic) acid, 3-phenylpropionic acid, trimethylacetic acid, tertiary butylacetic acid, lauryl sulfuric acid, gluconic acid, glutamic acid, hydroxynaphthoic acids, salicylic acid, stearic acid, muconic acid, and the like.

Preferred pharmaceutically acceptable salts are those formed with hydrochloric acid, sulfuric acid, phosphoric acid, acetic acid, methanesulfonic acid, ethanesulfonic acid, 1,2-ethanedisulfonic acid, 2-hydroxyethanesulfonic acid, benzene-sulfonic acid, p-chlorobenzenesulfonic acid, 2-naphthalenesulfonic acid, p-toluenesulfonic acid and camphorsulfonic acid.

Synthetic Reaction Parameters

Unless specified to the contrary, the reactions described herein take place at atmospheric pressure within a temperature range from 5° C. to 170° C. (preferably from 10° C. to 50° C.; most preferably at "room" or "ambient" temperature, i.e., about 20° to 30° C.). However, there are clearly some reactions where the temperature range used in the chemical reaction will be above or below these temperature ranges. Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20°–30° C.) over a period of about 1 to about 100 hours (preferably about 5 to 60 hours). Parameters given in the Examples are intended to be specific, not approximate. Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Presently Preferred Embodiments

While the broadest definition of this invention is set forth in the Summary of the Invention as a process for preparing the compound of Formula (I) and its pharmaceutically acceptable salts, the (R,S) mixture and certain salts are preferred.

The following acids are preferred to form pharmaceutically acceptable salts with the compound of Formula (I): hydrochloric, sulfuric, phosphoric, acetic, methanesulfonic, ethanesulfonic, 1,2-ethanedisulfonic, 2-hydroxyethanesulfonic, benzenesulfonic, p-chlorobenzenesulfonic, 2-naphthalenesulfonic, p-toluenesulfonic and camphorsulfonic acid. Most preferred are strong inorganic acids such as hydrochloric, sulfuric or phosphoric acid.

The most preferred compounds are 2-(2-amino-1,6-dihydro-6-oxo-purin-9-yl)methoxy-3-hydroxy-1-propyl-L-valinate hydrochloride and acetate. These compounds can be prepared as crystalline materials and therefore can be easily manufactured into stable oral formulations.

In any of the last step processes described herein, a reference to Formulae (I), (II), (III), (IV), (V), (VI), (VIa) or (VII) refers to such Formulae wherein $Z^1$, $Z^2$, $Z^3$, and $p^2$, A, $Y^1$, $Y^2$, Z and X are as defined in their broadest definitions set forth in the Summary of the Invention, with the processes applying particularly to the presently preferred embodiments.

Details of the Synthetic Processes

The process of the present invention is depicted in the Reaction Sequence shown below:

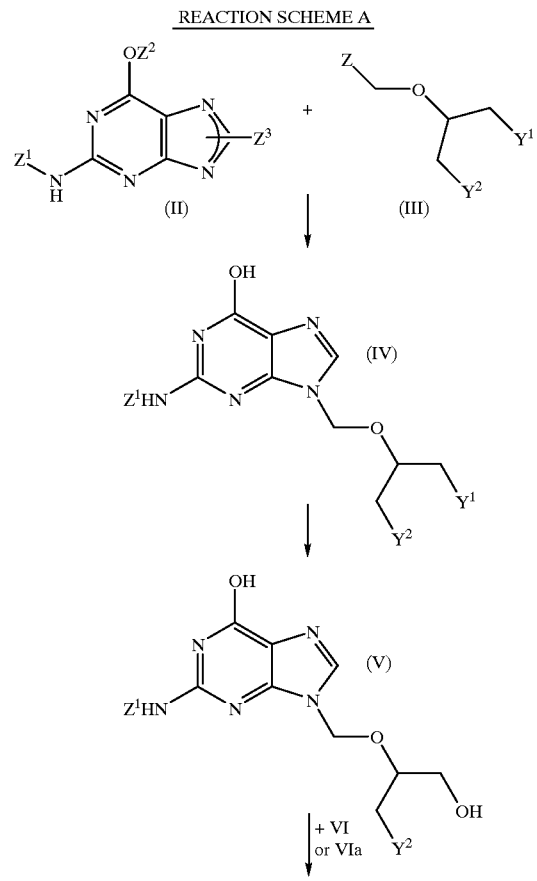

REACTION SCHEME A

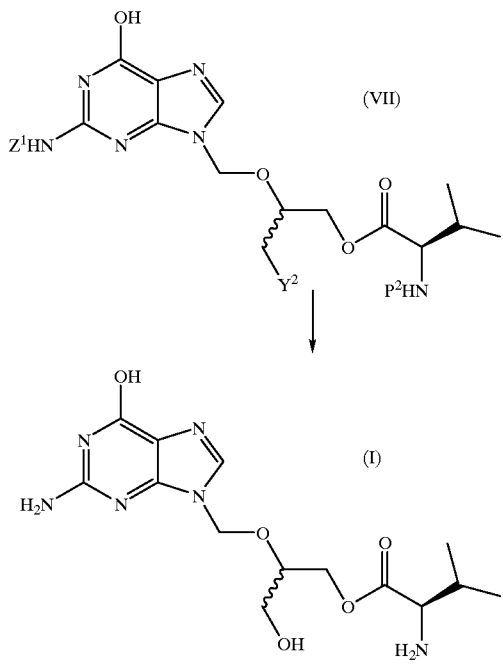

wherein $Z^1$, $Z^2$, and $Z^3$ are independently hydrogen or a silyl group of the formula —$SiR^5R^6R^7$, provided that at least one of $Z^1$, $Z^2$, and $Z^3$ must be a silyl group; optionally, $Z^1$ may be an amino-protecting group selected from the group consisting of lower alkanoyl, optionally substituted trityl, trifluoroacetyl and N-(9-fluorenylmethoxycarbonyl.

The compounds of Formula (III) are glycerol derivatives wherein $Y^1$ and $Y^2$ independently are halo, lower acyloxy, or aralkyloxy, or one of $Y^1$ or $Y^2$ is a valyloxy group, and Z is a leaving group selected from lower acyloxy, benzoyloxy, halo, mesyloxy or tosyloxy, and the like. In general, $Y^1$ and $Y^2$ of the glycerol derivative need to be chosen in such a way as to permit the obtention of the mono-L-valine ester of Formula (I). One of $Y^1$ or $Y^2$ can be an amino-protected L-valyloxy group, or a group convertible to the L-valyloxy group.

The guanine compound of Formula (II) is condensed with a 2-substituted glycerol of the Formula (III) to yield a compound of Formula (IV), which is a 2-(2-amino-1,6-dihydro-6-oxo-purin-9-yl) methoxy-1,3-propanediol (ganciclovir) intermediate with protection at both hydroxy functions (or protection at one hydroxy function when one of $Y^1$ or $Y^2$ is a valyloxy group) and optionally at the 2-amino group of guanine.

When both hydroxy functions are protected, the compound of Formula (IV) is then de-protected at one of the hydroxy functions to provide the mono-protected ganciclovir intermediate of Formula (V).

Optionally, a pharmaceutically acceptable acid addition salt of the compound of Formula (V) may be prepared. Preferred is the hydrochloride acid addition salt of Formula (V).

Compounds of Formula (V) may be esterified with an activated derivative of L-valine of Formula (VI) or (VIa) to provide the compounds of Formulae (VII), optionally followed by removal of amino- and/or hydroxy-protecting groups to form a compound of Formula (I).

If the valyloxy group is introduced in Step (a) using a glycerol derivative where one of $Y^1$ and $Y^2$ is an amino-protected L-valyloxy group or a group convertible to the L-valyloxy group, the resulting compound of Formula (IV) or (V) is converted directly to a compound of Formula (I) by removal of the hydroxy- and amino-protecting groups.

Compounds of Formula (I) can optionally be converted into a pharmaceutically acceptable salt thereof. The process can also include the conversion of an acid addition salt of the prodrug of Formula (I) into a non-salt form, the optical resolution of a compound of Formula (I) or the preparation of the compound of Formula (I) in crystalline form.

The present invention is an improved process for the preparation of mono-L-valine ganciclovir, in which the formation of the intermediate of Formula (V) provides distinct advantages over the previously known procedures. This novel intermediate may optionally be converted into an acid addition salt of a mono-hydroxy protected ganciclovir, which provides for a substantial reduction in several impurities which may be present in the commercially available guanine used to prepare the guanine derivative of Formula (II). These impurities may otherwise be carried through to the desired end-product.

In addition, the starting material for the preparation of some of the glycerol reagents of Formula (III) can be contaminated by certain impurities. These impurities are not removed during synthesis of the glycerol reagent, and when the reagent is reacted with guanine in the condensation reaction, it will give rise to the corresponding isomeric ganciclovir impurities. For example, the starting material for the glycerol reagent of Formula (III), wherein $Y^1$ is benzyloxy and $Y^2$ and Z are propionyloxy, can be the compound 1-benzyloxy-3-chloro-2-propanol. This starting material can contain 2-chloro-3-benzyloxypropanol or 2-benzyloxy-3-chloropropanol. Either of these impurities will give the corresponding impurity in the glycerol reagent and, in the ensuing condensation reaction with guanine, the impurity will carry through as an isomeric impurity of the ganciclovir intermediate.

Furthermore, the reaction of guanine with the glycerol reagent of Formula (III) gives a mixture of product isomers: the desired 9-substituted guanine (the 9-isomer) and a small amount of the undesired 7-substituted guanine (the 7-isomer). If the glycerol reagent contains the impurities discussed above, then the corresponding impurities of ganciclovir will also be present. None of these impurities can be removed easily from the desired 9-isomer.

The present invention provides for the optional generation of an acid addition salt of the compounds of Formula (IV) or (V), which allows for the isolation of the end-product essentially free of the 7-isomer and with levels of the impurities reduced by at least 50%. This acid addition salt intermediate can be prepared directly from the guanine reaction mixture which contains the dihydroxy-protected compound of Formula (IV). Alternatively, and in a preferred embodiment, the compound of Formula (IV) can be first deprotected at one of the hydroxy groups to provide the monohydroxy protected ganciclovir of Formula (V), from which intermediate the acid addition salt may then be prepared. Also, from the compound of Formula (IV), one can first prepare the intermediate with protection at both hydroxy moieties and at the 2-amino moiety of the guanine group with, for example, an acyl anhydride. This procedure is advantageous because the fully protected intermediate can be crystallized free of the undesired 7-isomer. These fully protected compounds are novel intermediates and are those compounds of the general Formula (IV), wherein $Z^1$ is an amino-protecting group which is lower acyl, $Y^1$ is halo, lower acyloxy or aralkyloxy, and $Y^2$ is lower acyloxy, so that the acyl groups of $Z^1$ and $Y^2$ are the same. A preferred, fully-protected intermediate is dipropionyl-monobenzyl ganciclovir or diacetyl-monobenzyl ganciclovir.

In general, the process for producing the compounds of Formula (I) may or may not involve protection of the amino group in the 2-position of the guanine base. These protecting groups may be removed prior to the formation of the salt intermediate of Formula (V), after the esterification step or in the last deprotection step. For the case when the ganciclovir intermediates have a protected 2-amino group the protecting group may be removed by conventional procedures. For example, if the amino-protecting group is a lower alkanoyl group, basic conditions (pH between 8 to 11) are employed to remove the protecting group. For example, a 2-N-acetyl-ganciclovir intermediate is treated with an alkaline reagent such as ammonium hydroxide, sodium or potassium carbonate or sodium or potassium hydroxide until the removal of the acetyl group is complete. In general, this reaction will be conducted in the presence of a suitable solvent such as a lower alkanol. Preferably the starting material is dissolved in methanol and a stoichiometric excess of ammonium hydroxide is added. The reaction temperature is kept between 0° to 50° C., preferably at room temperature. After the reaction is complete (which can be determined by TLC), another solvent may be added to facilitate isolation of the de-protected product, such as ethyl ether which leads to precipitation of the de-acylated product which can be filtered off and isolated using conventional separation methods.

In general, when carrying out a process of this invention, those amino, hydroxy or carboxylic groups which are not to participate in the synthesis reaction must be protected until (1) either de-protection yields the final product; or (2) the presence of the unprotected group in the ensuing reaction steps leading to the final product would not modify the intended sequence of reactions. An example for meeting requirement (1) is the benzyloxycarbonyl group in the preparation of the final product of this invention, which protects the amino group of the valine function of ganciclovir until it is removed in the de-protection step. An example for meeting requirement (2) is the acetyl group, or the trityl or monomethoxytrityl group protecting the amino group of the guanine ring system of ganciclovir, as the unprotected amino group does not interfere with the esterification (Step c).

In general, the qualification of potential blocking agents that render them suitable for use in the preparation of the compound of Formula (I) include:

(1) Their introduction should proceed quantitatively and smoothly without L-valine racemization;

(2) The blocked intermediate must be stable to conditions of the reactions employed until removal of the protecting group is required;

(3) The blocking group must be susceptible of being readily removed under conditions which do not change the chemical nature of the remainder of the molecule or result in racemization of the L-valine component.

REACTION SCHEME B

Silylation/Persilylation of Guanine

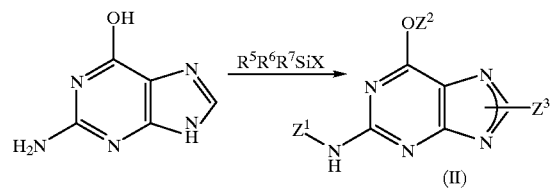

where $Z^1$, $Z^2$ and $Z^3$ are independently hydrogen or a silyl protecting group of the formula $R^5R^6R^7Si$, in which $R^5$, $R^6$, and $R^7$ are independently lower alkyl, provided that at least one of $Z^1$, $Z^2$ and $Z^3$ is a silyl group.

Preparation of Silylated/Persilylated Guanine of Formula (II)

The trialkylsilyl halides of formula $R^5R^6R^7SiX$ (where X is chloro or bromo) or hexamethyldisilazane are commercially available.

As illustrated in Reaction Scheme B, guanine is silylated to give the corresponding protected compound of Formula (II).

The protection of guanine is well known in the art (see, for example "Synthesis of 9-substituted Guanines. A review" by F. P. Clausen and J.J. Christensen, Org. Prep. Proced. Int., 25(4), pp 375–401 (1993)). Guanine may, for example, be protected using acyl groups, for example acetyl, or by silyl groups. Traditionally, when silyl groups are employed for protection, guanine is silylated in such a manner that all active protons present in guanine are replaced by a silyl group before proceeding with the desired reaction, i.e. guanine is protected as the trisilyl derivative. However, it has been found that, although trisilylation of guanine followed by the condensation of Step (a) gives the desired product in good yield, and indeed is preferred, it is not essential that guanine be trisilylated for the condensation carried out in Step (a) to be essentially specific for the preparation of compound (IV). Conventionally, guanine as a slurry is reacted with a silylating agent, for example hexamethyldisilazane, at reflux until all suspended material goes into solution, which signals the complete formation of the trisilyl derivative. This reaction can take up to 48 hours or more. It has been found that refluxing for much less time, for example as little as 2 hours, then reacting the slurry thus produced with a compound of Formula (III) as described in Step (a), gives good yields of desired product. This result is clearly advantageous, since less expense is involved in a shortened reaction time, and smaller amounts of silylating reagent are used. Although the composition of a compound of Formula (II) produced by reacting guanine with hexamethyldisilazane for a shortened period of time is not yet known with any certainty, it is believed to be mainly a monosilyl derivative, probably mixed with some disilyl and trisilyl guanine.

In one preferred method, guanine is reacted with about 3–10 molar equivalents of a silylating agent, preferably with hexamethyldisilazane (i.e. to give a compound of Formula (II) where $R^5$, $R^6$, and $R^7$ are all methyl), in the presence of an silylation catalyst, preferably ammonium sulfate, trifluoromethanesulfonic acid, trimethylsilyltrifluoromethane sulfonate, or bistrimethylsilyl sulfonate, most preferably trifluoromethanesulfonic acid (about 0.01 to 0.1 molar equivalents). The mixture is heated to reflux over a period of about 5–24 hours, preferably about 16 hours. When the reaction is substantially complete, excess silylating agent is removed under reduced pressure, and the resultant solution of the protected guanine product of Formula (II) is used in the next step without further purification.

Alternatively, guanine is reacted with a silylating agent, preferably hexamethyldisilazane, in the presence of a silylating catalyst, preferably trifluoromethanesulfonic acid, as described in the preceding paragraph, but for a period of about 1–8 hours, preferably 2–4 hours. Optionally, excess silylating agent is removed under reduced pressure, and the resultant mixture of the protected guanine product of Formula (II) is used in the next step without further purification.

Alternatively, guanine may be reacted with 1–5 molar equivalents of a trialkylsilyl halide of formula $SiR^5R^6R^7X$, in which $R^5$, $R^6$, and $R^7$ are independently lower alkyl and X is chloro or bromo, such as trimethylsilyl chloride, tert-butyl-dimethylsilyl chloride, and the like, in the presence of about 1–5 molar equivalents of a base.

It should be noted that ammonium sulfate, trifluoromethanesulfonic acid, trimethylsilyltrifluoromethane sulfonate, or bistrimethylsilyl sulfonate work well as silylation catalysts in the silylation of guanine described above. However, use of trifluoromethanesulfonic acid is preferred because it is much less expensive than trimethylsilyltrifluoromethane sulfonate or bistrimethylsilyl sulfonate.

Starting Materials

All starting materials employed to make the compound of Formula (I) are known, such as guanine and the protecting and carboxylic-group-activating reagents.

The glycerol derivatives of Formula (III) which are used in the condensation reaction with guanine or a protected guanine compound are described in European Patent Applications 0 694 547 A and 0 187 297. European Patent Application 0 187 297 also describes certain methods for preparing the glycerol derivatives of Formula (III). A preferred method for preparing the glycerol derivatives is described below in the section "Preparation of Glycerol Derivatives".

A preferred guanine derivative is the silylated/persilylated guanine. Preferred glycerol derivatives are 1-benzyloxy-3-propionyloxy-2-(propionyloxy)methoxypropane, 1-benzyloxy-3-acetyloxy-2-(acetyloxy)methoxypropane, or 1-benzyloxy-3-benzyloxy-2-(acetyloxy)methoxypropane.

Prior to carrying out Step (c) (esterification step), the amino group of the L-valine derivative must be protected to avoid its interference with the esterification by undesirable amide formation. The various amino-protected L-valine derivatives useful in this invention, such as N-benzyloxycarbonyl-L-valine, BOC-L-valine and FMOC-L-valine, N-formyl-L-valine and N-benzyloxycarbonyl-N-carboxy-L-valine anhydride, are all commercially available (SNPE Inc., Princeton, N.J., Aldrich Chemical Co., Milwaukee, Wis., and Sigma Chemical Co., St. Louis, Mo.), or are described in the literature, such as N-allyloxycarbonyl-L-valine. Cyclic amino-protected L-valine derivatives are also described in the literature, as noted above. Of particular interest for the present invention is the benzyloxycarbonyl valine-substituted 2-oxa-4-aza-cycloalkane-1,3-dione (Z-valine-N-carboxyanhydride, or Z-Valine-NCA), which is also commercially available (SNPE Inc., Princeton, N.J.). Alternatively, the protecting step may be carried out by conventional methods.

Preparation of Glycerol Derivatives of Formula (III)

The glycerol derivatives useful in this invention can be prepared from known starting materials. For example, the compounds of Formula (III) wherein $Y^1$ is lower aralkyloxy or halo, $Y^2$ is lower acyloxy or halo, and Z is lower acyloxy, can be prepared as described below. This reaction is exemplified by the preparation of the compounds wherein $Y^1$ is benzyloxy, $Y^2$ is propionyloxy and Z is propionyloxy, i.e., 1-benzyloxy-3-propionyloxy-2-(propionyloxy) methoxypropane.

Epichlorohydrin is reacted with benzyl alcohol in the presence of tetrabutylammonium bisulfate in aqueous sodium hydroxide, at room temperature. The product of this reaction, benzyl glycidyl ether, is isolated by conventional means and is then added slowly to a suspension of lithium chloride in tetrahydrofuran and acetic acid, at 40°–70° C., preferably below 60° C. The reaction mixture is allowed to cool to room temperature, and stirred for 2–10 hours, preferably 3–6 hours. The product is isolated by extraction, washed and dried to provide 1-benzyloxy-3-chloro-2-propanol. To this product is then added methoxymethyl propionate, which is prepared by adding propionic anhydride to dimethoxymethane in the presence of an ion exchange resin, e.g., Amberlyst 15, maintaining the temperature between 40°–60° C., preferably between 40°–50° C. during the addition. The reaction mixture is aged and cooled, then filtered, washed and distilled. This product, methoxymethyl propionate, is reacted with 1-benzyloxy-3-chloro-2-propanol in an aprotic solvent, e.g., hexanes, in the presence of p-toluenesulfonic acid hydrate at reflux. Distillation and washing affords the product 1-benzyloxy-3-chloro-2-(propionyloxy)methoxypropane. Finally, to prepare the compounds of Formula (III), 1-benzyloxy-3-chloro-2-(propionyloxy)methoxypropane, is refluxed with an alkali metal alkanoate, e.g., sodium propionate, in an aprotic solvent, e.g., toluene, after which a phase transfer catalyst such as tetrabutylphosphonium chloride is added. The reaction mixture is stirred at 90° C. to reflux temperature for 1–3 days, preferably 2 days, at which time more tetrabutylphosphonium chloride and solvent may be added, if required. The mixture is heated to reflux and the distillate removed, then stirred at 90° C. to reflux temperature for 3–16 hours, preferably 5–10 hours, then cooled to ambient temperature. The mixture is then washed with water and brine, and the organic phase is separated and concentrated to yield 1-benzyloxy-3-propionyloxy-2-(propionyloxy)methoxy propane. In an analogous manner, other glycerol derivatives of Formula (III) may be prepared.

Further nonlimiting examples of phase transfer catalysts or agents that may be employed in the preparation of compounds of Formula (III) are reviewed by C. M. Starks, C. L. Liotta, and M. Halpern in "Phase-Transfer Catalysis", Chapman & Hall, New York, 1994, which is incorporated herein in its entirety by reference.

Preparation of Activated Derivative of L-valine

Prior to carrying out Step (c) (esterification step), L-valine must also be activated. At least 1 equivalent of the protected amino acid and 1 equivalent of a suitable coupling agent or dehydrating agent, for example 1,3-dicyclohexylcarbodiimide or salts of such diimides with basic groups should be employed from the start. Other carbodiimides such as N,N'-carbonyldiimidazole may also be used. Further useful dehydrating agents are trifluoroacetic anhydride, mixed anhydrides, acid chlorides, 1-benzotriazolyloxy-tris-(dimethylamino)phosphonium hexafluorophosphate, benzotriazol-1-yl-oxy-trispyrrolidinophosphonium hexafluorophosphate, 1-hydroxybenzotriazole, 1-hydroxy-4-azabenzotriazole, 1-hydroxy-7-azabenzotriazole, N-ethyl-N'-(3-(dimethylamino) propyl)carbodiimide hydrochloride, 3-hydroxy-3,4-dihydro-4-oxo-1,2,3-benzotriazine, O-(benzotriazol-1-yl)-1,1,3,3-tetramethyluronium hexafluorophosphate, O-(7-azabenzotriazol-1-yl)-1,1,3,3- tetramethyluronium hexafluorophosphate, O-(7-azabenzotriazol-1-yl)-1,1,3,3-tetramethyluronium tetrafluoroborate, O-(1H-benzotriazol-1-yl)-1,1,3,3-bis(tetramethylene) uronium hexafluorophosphate or O-(7-azabenzotriazol-1-yl)-1,1,3,3-bis-(tetramethylene)uronium hexafluorophosphate.

A description of these coupling agents by L. A. Carpino can be found in J. Am. Chem. Soc. 1993, 115, p. 4397–4398.

Also useful for this purpose are urethane-protected amino acid N-carboxy anhydrides (UNCA's) which are an activated form of an amino acid; these have been described by William D. Fuller et al., J. Am. Chem. Soc. 1990, 112, 7414–7416, which is incorporated herein by reference. Other protected amino acid N-carboxy anhydrides are described in PCT Patent Application WO 94/29311, discussed above. In summary, any other reagent that produces an anhydride or another activated derivative of the protected amino acid under mild conditions can be used as the coupling agent.

The amino-protected amino acid is dissolved in an inert solvent such as a halogenated lower alkane, preferably dichloromethane, under an inert atmosphere, for example nitrogen, and the coupling agent is added (preferably 1,3-dicyclohexylcarbodiimide). The reaction mixture is stirred at temperatures between 0° and 50° C., preferably at about room temperature. The reaction mixture is filtered and the reaction product (the anhydride of the protected amino acid) isolated. The resulting product is dissolved in a dry inert solvent such as dry dichloromethane and placed under nitrogen.

Preparation of Mono-L-valine Ganciclovir

Step (a): Condensation

The reaction conditions for the condensation of guanine with the 2-amino group optionally protected, are described in European Patent Application 0 187 297. In this condensation reaction, guanine is reacted with a glycerol derivative of Formula (III) in an aprotic hydrocarbon solvent (such as benzene, toluene or xylenes) or dimethylformamide with a hexa-lower alkyl(di)silazane, for example, hexamethyldisilazane, hexaethyldisilazane, or the like, and a catalyst at temperatures between 30° C. and reflux temperature. The catalyst is a Lewis acid salt such as trialkyl silyl salt (e.g., the sulfate), or a trifluoroalkyl sulfonic acid, a chlorosilane, or ammonium sulfate and pyridine. For a more detailed disclosure of the reaction conditions for condensation (Step (a)) see the disclosure of European Patent Application 0 187 297 which is incorporated herein by reference. The resulting compound is a ganciclovir derivative with protected hydroxy groups and with an optionally protected 2-amino group.

For example, a ganciclovir intermediate of Formula (IV), where $Y^1$, is benzyloxy and $Y^2$ is lower acyloxy, can be prepared by condensing persilyl guanine with a glycerol derivative of Formula (III) where $Y^1$ is benzyloxy and $Y^2$ and Z are lower acyloxy. Typically, persilyl guanine is treated with a large excess of a glycerol derivative of Formula (III) in the presence of a catalytic amount of a Lewis acid salt, preferably trifluoromethane sulfonic acid at 60°–150° C. preferably 110°–130° C. for 3–24 hours, preferably 6–8 hours. The mixture is cooled, diluted with an aprotic non-polar solvent, preferably toluene, and then water is added carefully. The product can optionally be isolated by filtration.

Step (b): Hydrolysis

The protected ganciclovir derivative of Formula (IV) from Step (a) is partially de-protected to provide ganciclovir with the 2-amino group optionally in protected form and one protected primary hydroxyl function. Preferably, the primary hydroxyl function is protected with a benzyl group. Suitable amino-protecting groups are lower alkanoyl groups with 2 to 4 carbon atoms, in particular the acetyl or propionyl group. Other suitable amino-protecting groups are the trityl or substituted trityl groups such as the monomethoxytrityl group, and the 4,4'-dimethoxytrityl group.

As noted above, the acid addition salt of the compound of Formula (V), can be prepared directly from the product of Step (a), which is the dihydroxy-protected compound of Formula (IV), by de-protecting one of the hydroxy groups with concomitant preparation of the salt. Alternatively, the compound of Formula (IV) can first be deprotected at one of the hydroxy groups to provide the mono-hydroxy protected ganciclovir of Formula (V), from which the acid addition salt is then prepared. Also, the compound of Formula (IV), the intermediate with protection at both hydroxy groups as well as at the 2-amino guanine group can be prepared, with, for example, an acyl anhydride. For example, the dipropionyl monobenzyl ganciclovir intermediate is prepared from the propionyl monobenzyl ganciclovir intermediate of Formula (IV) by reaction with propionic anhydride/dimethylaminopyridine, in, for example, toluene. As discussed above, the ganciclovir intermediate with protection at both hydroxy groups and at the 2-amino guanine group, such as dipropionyl monobenzyl ganciclovir, is a preferred intermediate because it can be isolated substantially free of the undesired 7-isomer of guanine.

When one of $Y^1$ and $Y^2$ is aralkyloxy, or when both $Y^1$ and $Y^2$ are aralkyloxy, for example, benzyloxy, then deprotection occurs by hydrogenolysis under conventional hydrogenation conditions; when one of the groups $Y^1$ or $Y^2$ is acyloxy or halo, said group is selectively removed by basic hydrolysis.

Transfer hydrogenation conditions can also be employed: a palladium catalyst such as palladium hydroxide is used in a suitable solvent such as cyclohexene. A cosolvent such as methanol, ethanol or isopropanol may be necessary for better solubility of the adduct.

Hydrogenolysis is preferably carried out by dissolving the protected ganciclovir in a solvent system under conventional hydrogenation conditions at 5–100 psi (0.3–7 atm), preferably 10–40 psi (0.7–2.8 atm) hydrogen, in the presence of a catalyst such as a palladium compound, in particular palladium hydroxide on carbon (Pearlman's catalyst), at about 20°–60° C., preferably 20°–35° C., until completion of the reaction. Other suitable hydrogenation catalysts include hydrogenation catalysts in general such as Pd, Pd on carbon and homogeneous hydrogenation catalysts. The solvent system includes a lower alkanol such as methanol or ethanol. Generally the reaction will be carried out at temperatures between room temperature and the reflux temperature of the solvent system, for example in refluxing ethanol under a hydrogen atmosphere and under exclusion of air. The reaction vessel is preferably swept with nitrogen prior to charging it with hydrogen. The catalyst will be recovered by filtration. The filtrate can be reduced in volume by evaporation of excess solvent. The resulting crude reaction mixture generally includes unchanged starting material and 2-amino-protected ganciclovir with one aliphatic hydroxy group protected as the major products. The separation of these two products is usually performed by isolation procedures known in the art, often by chromatographic methods, preferably on silica gel, followed by elution with appropriate eluents such as mixtures of a lower alkanol with a halogenated lower alkane (preferably ethanol and dichloromethane) to give 2-amino-protected ganciclovir with one aliphatic hydroxy group protected. This ganciclovir intermediate can then be isolated as the salt compound of Formula (V) by conventional methods, using, for example, hydrogen chloride and a solvent such as methanol.

The hydrolysis reaction to remove an acyl hydroxy-protecting group is preferably carried out by treating the protected ganciclovir under basic hydrolysis conditions. The hydrolysis medium may include a lower alkyl alcohol such as methanol or ethanol, toluene, and aqueous sodium hydroxide. Generally the reaction will be carried out at temperatures between room temperature and the reflux temperature of the solvent system. Again, this ganciclovir intermediate can be isolated as the salt compound of Formula (V) as described above.

For example, the product obtained in Step (a) can be partially deprotected by removing the lower acyl group (of $Y^1$ or $Y^2$) with base. After the reaction described in Step (a) is complete and the reaction mixture has been cooled and diluted with, preferably, methanol, aqueous sodium hydroxide is added. The mixture is heated to 40°–90° C., preferably 60°–80° C., until the reaction is complete. The reaction mixture is then carefully acidified with hydrochloric acid. The product is collected as the hydrochloride salt by filtration, then washed and dried.

Step (c): Esterification

In this step an activated derivative of amino-protected L-valine of the Formula (VI) or (VIa) is esterified with the mono-hydroxy protected ganciclovir salt derivative of Formula (V) obtained in Step (b). Suitable amino-protecting groups for the L-valine derivative are the N-benzyloxycarbonyl group, the phthalyl group, the tertiary butyloxycarbonyl group and the N-(9-fluorenylmethoxycarbonyl) or "FMOC" group.

A suspension of the product of Step (b)(the compound of Formula (V) in an aprotic solvent (preferably dimethylformamide) containing an organic base (preferably TEA) is added to an approximately equivalent amount of the activated L-valine derivative in an aprotic solvent (preferably dimethylformamide). The activated L-valine derivative is preferably Z-valine-N-carboxyanhydride or L-valine anhydride. The reaction mixture is stirred at 0°–40° C., preferably at 4°–10° C., for 1–5 hours. The reaction mixture is diluted with water, preferably toluene and water. The precipitate is collected by filtration, washed and dried at ambient temperature.

Step (d): Final De-protection to Give the Product of Formula (I)

The valine protecting groups of the product of Step (c), the hydroxy protecting group $Y^2$ and optionally any 2-amino guanine protecting groups are removed by de-protection reactions, preferably in an acidic medium or solvent, most preferably by hydrogenation. De-protection under acidic conditions is preferred, as this will ensure that the amino group liberated in the de-protection reaction will be protonated; that is, that the base of Formula (I) as it is formed in the de-protection reaction will be captured by an at least stoichiometric amount of acid present. Isolating the compound of Formula (I) as an acid addition salt will protect the desired stereoconfiguration of the compound of Formula (I). Therefore, those examples given below that show the de-protection step also show the concomitant salt formation step.

The de-protection reaction is carried out by dissolving the product of the esterification step (c) in an inert solvent, preferably in an acidic solvent, using a hydrogenation catalyst such as palladium on carbon, or palladium hydroxide on carbon (Pearlman's catalyst), using elevated hydrogen pressure between 1 and 2000 psi (0.1–140 atm), preferably 20 to 200 psi (1.4–14 atm). The completion of the reaction can be monitored using conventional TLC analysis. The hydrogenolysis is continued until the conversion is complete, if required with addition of further hydrogenation catalyst. The catalyst is removed and washed. The combined filtrates from filtration and the washings are concentrated and lyophilized to isolate the ganciclovir L-valine ester. The purification of the product and the isolation of a crystalline ester is carried out by recrystallization or other purification techniques such as liquid chromatographic techniques.

The hydrogenolysis may be slow due to the presence of impurities (catalyst poisons) in the starting material. It has been found to be advantageous to treat the starting material prior to hydrogenolysis in methanol with filtering aids such as catalytic Filtrol®, Solka Floc® and activated carbon such as ADP carbon. This effectively removes most catalyst poisons.

If the tertiary butyloxycarbonyl group is being used as amino-protecting group, its removal is effected with acid such as HCl and isopropanol as a solvent or with trifluoroacetic acid neat.

Alternatively, if the esterification step has been carried out with a trityl or substituted trityl-protected ganciclovir derivative, such protecting groups can be removed by treatment with an aqueous alkanoic acid or trifluoroacetic or hydrochloric acid at temperatures between −20° C. and 100° C., for example, aqueous acetic acid.

Preparation of Salts

One of ordinary skill in the art will also recognize that the compound of Formula (I) may be prepared either as an acid addition salt or as the corresponding free base. If prepared as an acid addition salt, the compound can be converted to the free base by treatment with a suitable base such as ammonium hydroxide solution, sodium hydroxide, potassium hydroxide or the like. However, it is important to point out that the free base of Formula (I) is more difficult to characterize than its acid addition salts. When converting the free base to an acid addition salt, the compound is reacted with a suitable organic or inorganic acid (described earlier). These reactions are effected by treatment with an at least stoichiometric amount of an appropriate acid (in case of the preparation of an acid addition salt) or base (in case of liberation of the free compound of Formula (I)). In the salt-forming step of this invention typically, the free base is dissolved in a polar solvent such as water or a lower alkanol (preferably isopropanol) or mixtures thereof, and the acid is added in the required amount in water or in lower alkanol. The reaction temperature is usually kept at about 0° to 50° C., preferably at about room temperature. The corresponding salt precipitates spontaneously or can be brought out of the solution by the addition of a less polar solvent such as ether or hexane, removal of the solvent by evaporation or under vacuum, or by cooling the solution.

Isolation of Stereoisomers and the Manufacture of Crystalline 2-(2-Amino-1,6-dihydro-6-oxo-purin-9-yl)methoxy-3-hydroxy-1-propyl-L-valinate From the Formula (I) it is apparent that the compound of the invention has one asymmetric carbon atom (chiral center) in the propyl chain, in addition to the asymmetric carbon atom in L-valine. Therefore, two diastereomeric forms exist, the (R)- and (S)- form as determined by the rules of Cahn et al. Suitable methods for the separation of the diastereomers are described in European Patent Application 0 694 547 A, incorporated herein by reference.

The compounds of Formula (I) may also be prepared in crystalline form, which has many well-known advantages over the non-crystalline form. Suitable methods for the preparation of the compounds of the invention in crystalline form are also described in European Patent Application 0 694 547 A, incorporated herein by reference.

The following preparations and examples are given to enable those skilled in the art to more clearly understand and to practice the present invention. They should not be considered as limiting the scope of the invention, but merely as being illustrative and representative thereof.

EXAMPLE 1

1A. Preparation of 2-(2-amino-1,6-dihydro-6-oxo-purin-9-yl)methoxy-3-benzyloxy-1-propyl-propionate Trifluoromethane sulfonic acid (0.5 ml) was added to guanine (25 g) and the mixture was briefly agitated. Hexamethyldisilazane (HMDS) (125 ml) was added and the mixture was heated to reflux until solution was achieved. The solution was vacuumed distilled to remove excess HMDS. The residue was cooled and more trifluoromethane sulfonic acid (0.4 ml) was added, followed by 1-benzyloxy-3-propionyloxy-2-(propionyloxy)methoxypropane (70 g). The mixture was heated at 110°–130° C. for several hours until little or no guanine was detected by HPLC. The mixture was cooled and diluted with toluene (150 ml) and methanol (21 ml). Water (20 ml) was added carefully and the mixture was then cooled. Propionyl monobenzyl ganciclovir (29 g) was collected by filtration, washed with toluene and water and dried.

1B. Preparation of 2-(2-amino-1,6-dihydro-6-oxo-purin-9-yl)methoxy-3-benzyloxy-1-propyl-acetate Trifluoromethane sulfonic acid (0.5 ml) was added to guanine (25 g) and the mixture was briefly agitated. Hexamethyldisilazane (HMDS) (125 ml) was added and the mixture was heated to reflux until solution was achieved. The solution was vacuumed distilled to remove excess HMDS. The residue was cooled and more trifluoromethane sulfonic acid (0.4 ml) was added followed by 1-benzyloxy-3-acetyloxy-2-(acetyloxy)methoxypropane (65 g). The mixture was heated at 110°–130° C. for several hours until little or no guanine was detected by HPLC. The mixture was cooled and diluted with toluene (75 ml). Water (25 ml) was added carefully and the mixture was then cooled. Acetyl monobenzyl ganciclovir (38 g) was collected by filtration, washed with toluene and water and dried.

1C. Preparation of 2-(2-acetylamino-1,6-dihydro-6-oxo-purin-9-yl)methoxy-1,3-dibenzyloxy-propane In a completely analogous manner to that described in Examples 1A and 1B, 2-(2-acetylamino-1,6-dihydro-6-oxo-purin-9-yl)methoxy-1,3-dibenzyloxy-propane was prepared using 1-benzyloxy-3-benzyloxy-2-acetyloxymethoxypropane as the glycerol reagent and 2-N-acetyl-guanine.

EXAMPLE 2

Preparation of 2-(2-amino-1,6-dihydro-6-oxo-purin-9-yl) methoxy-3-benzyloxy-1-propanol hydrochloride 2A. The preparation of the mono-protected ganciclovir intermediate as a salt (the compound of Formula V) was prepared directly from the product of Example 1A.

Monobenzyl ganciclovir hydrochloride was isolated as the product of the procedure described in Example 1A by using the following modification: After the reaction was complete and was cooled and diluted with methanol (250 ml), NaOH (23 g) was added. The mixture was heated with good agitation. When hydrolysis was judged complete (HPLC, TLC), the mixture was cooled and conc. hydrochloric acid (45.2 g) added. The mixture was filtered and the filtrate diluted with ethyl acetate (240 ml). The mixture was cooled and the product collected, washed with ethyl acetate and dried to yield 30.0 g.

2B. Similarly, monobenzyl ganciclovir hydrochloride was prepared from acetylmonobenzyl ganciclovir (the product of Example 1B) by heating a mixture of sodium hydroxide (10.0 g), methanol (150 ml) and acetylmonobenzyl ganciclovir (49 g) until the reaction was complete. The solution was acidified with hydrochloric acid (31 g) and the mixture was filtered. The filtrate was diluted with ethyl acetate (750 ml) and cooled. The product was collected by filtration, washed with ethyl acetate and dried to yield 47 g.

EXAMPLE 3

Preparation of 2-(2-amino-1,6-dihydro-6-oxo-purin-9-yl) methoxy-3-benzyloxy-1-propanol hydrochloride 3A. The preparation of the mono-protected ganciclovir intermediate as a salt (the compound of Formula V) was also prepared via the non-salt intermediate (2-(2-amino-1,6-dihydro-6-oxo-purin-9-yl)methoxy-3-benzyloxy-1-propanol, or monobenzyl ganciclovir.

Monobenzyl ganciclovir was isolated as the product of the procedure described in Example 1A by using the following modification: After the reaction was complete and was cooled and diluted with toluene (25 ml), a solution of NaOH (25 g) in water (125 ml) was added. The mixture was heated with good agitation. When hydrolysis was judged complete (HPLC, TLC), the lower aqueous layer was slowly added to a hot mixture of acetone (125 ml), acetic acid (25 g) and water (25 ml) with good agitation. The mixture was cooled and monobenzyl ganciclovir isolated by filtration, washed with aqueous acetone and dried.

Next, monobenzyl ganciclovir hydrochloride was prepared from monobenzyl ganciclovir (17 g) by mixing with conc. hydrochloric acid (5 ml) and methanol (80 ml) and warming until all solid dissolved. The solution was diluted with ethyl acetate (160 ml) and cooled. The product was collected by filtration, washed with ethyl acetate and dried to yield 18.1 g.

While a preferred solvent for preparing monobenzyl ganciclovir hydrochloride from monobenzyl ganciclovir is methanol, other solvents can be used in an analogous manner. Such other solvents include isopropanol, ethanol and butanol.

3B. Alternatively, monobenzyl ganciclovir and monobenzyl ganciclovir hydrochloride were prepared from the product of Example 1B.

Monobenzyl ganciclovir was isolated as the product of the procedure described in Example 1B by using the following modification: After the reaction was complete and was cooled and diluted with toluene (25 ml), a solution of NaOH (25 g) in water (125 m) was added. The mixture was heated with good agitation. When hydrolysis was judged complete (HPLC, TLC), the lower aqueous layer was slowly added to a hot mixture of acetone (125 ml), acetic acid (25 g) and water (25 ml) with good agitation. The mixture was cooled and monobenzyl ganciclovir isolated by filtration, washed with aqueous acetone and dried to yield 41 g.

Monobenzyl ganciclovir HCl was then prepared from monobenzyl ganciclovir in a manner similar to that described in Example 3A, above.

3C. Alternatively, monobenzyl ganciclovir and monobenzyl ganciclovir hydrochloride were prepared from the product of Example 1C. In this example, the product of Example 1C is a 2-amino protected dibenzyl ganciclovir intermediate of Formula (IV).

First, N-acetyl-dibenzyl-ganciclovir was converted to N-acetyl-monobenzyl-ganciclovir. N-acetyl-dibenzyl-ganciclovir (14.5 Kg) was charged to a 200 liter glass reactor along with 60.1 Kg methanol, and 900 g of Pearlman's catalyst. This mixture was placed under a hydrogen atmosphere and heated to 40° C. for 11 hours. The catalyst was removed by filtration through a Solka Floc® cake. This cake was washed with 60 Kg of methanol. Methanol (60 kg) was distilled from the solution of N-acetyl-dibenzyl-ganciclovir and N-acetyl-monobenzyl-ganciclovir. Water (113 kg) was added to this concentrated methanol solution. This mixture was cooled to 5° C. overnight. The N-acetyl-dibenzyl-ganciclovir was then removed by filtration and washed with 140 L of (6:4) methanol/water. The methanol/water solutions were combined and methanol/water was distilled under vacuum to a jacket temperature of 115° C., 27 ins of Hg (ca. 685 torr), and a pot temperature of 44° C., until 260 Kg of methanol/water had distilled. The resulting aqueous layer was extracted 3 times with 100 kg each of dichloromethane (each dichloromethane extraction contained 3.75 L ethanol.) The dichloromethane layers were combined and the dichloromethane/ethanol was removed by atmospheric distillation to a pot temperature of 40° C. Acetone (7.3 L) was added to the pot residue and the pot was heated to 50° C. with agitation. This heterogeneous mixture was cooled to 5° C. overnight. The solid was filtered out and washed with 15 L (−5° C. to −10° C. The solid was dried in a vacuum oven (~50° C. 25 ins of Hg (ca. 635 torr), nitrogen sweep) for 24 hours. Isolated yield of N-acetyl monobenzyl-ganciclovir: 29% (3.425 Kg). HPLC: 91.7% N-acetyl-monobenzyl ganciclovir, 2.3% monobenzyl ganciclovir, 0.3% N-acetyl-ganciclovir.

Ammonolysis of N-acetyl-monobenzyl ganciclovir to monobenzyl-ganciclovir: To 103 g N-acetyl-monobenzyl-ganciclovir was added 500 ml methanol and 100 ml 30% NH$_4$OH in water. The reaction was complete by TLC in about 22 hours. The methanol was evaporated from the heterogeneous mixture to a temperature of 40° C., at 28 ins of Hg (ca. 710 torr). The aqueous solution was cooled to room temperature, and then filtered. The solid was washed with 500 ml water and dried in a vacuum oven (~50° C., 25 ins of Hg (ca 635 torr), nitrogen sweep) overnight. Weight: 94.1 g (7179–94). HPLC: 95.5% monobenzyl ganciclovir.

Monobenzyl ganciclovir HCl was then prepared from monobenzyl ganciclovir in a manner similar to that described in Example 3A, above.

EXAMPLE 4

Preparation of 2-(2-amino-1,6-dihydro-6-oxo-purin-9-yl) methoxy-3-benzyloxy-1-propanol hydrochloride 4A. The preparation of the mono-protected ganciclovir intermediate as a salt (the compound of Formula V) was also prepared via a 2-amino protected intermediate 2-(2-propionyl-amino-1,6-dihydro-6-oxo-purin-9-yl)methoxy-3-benzyloxy-1-propyl propionate.

Dipropionylmonobenzyl ganciclovir was isolated as the product of the procedure described in Example 1A by using the following modification: After the reaction was complete and was cooled a solution of 4-dimethyl- aminopyridine (1.6 g) in propionic anhydride (31 g) was added and the mixture was heated until the acylation was complete (HPLC, TLC). Water (8.5 ml) was added and the hot mixture was extracted-with hexane (160 ml)or a hexane (160 ml)/toluene (80 ml) mixture. The lower layer of the mixture was separated and diluted with toluene (150 ml). The hot solution was washed with water (1×25 ml , 1×75 ml), diluted with ethyl acetate (15 ml), and again washed with water (75 ml). The organic layer was cooled and stirred. The product was collected by filtration, washed with toluene and dried to yield 43 g.

Monobenzyl ganciclovir hydrochloride was prepared from dipropionylmonobenzyl ganciclovir by heating a mixture of sodium hydroxide (20.0 g), methanol (400 ml) and dipropionylmonobenzyl ganciclovir (112 g) until the reaction was complete. The solution was acidified with hydrochloric acid (73.5 g) and the mixture was filtered. The filtrate was diluted with ethyl acetate (800 ml)and cooled. The product was collected by filtration, washed with ethyl acetate and dried to yield 76.7 g monobenzyl ganciclovir hydrochloride.

4B. Monobenzyl ganciclovir was also prepared from dipropionylmonobenzyl ganciclovir as follows: A mixture of sodium hydroxide (7 g), water (80 ml)and dipropionyl-monobenzyl ganciclovir (22.9 g) was heated until the reaction was complete. The mixture was added to a mixture of acetic acid (10 g) and water (20 ml)and was then cooled. The product was collected by filtration, washed with water and dried to yield 17.1 g.

EXAMPLE 5

Preparation of 2-(2-amino-1,6-dihydro-6-oxo-purin-9-yl) methoxy-3-benzyloxy-1-propyl-N-(benzyloxycarbonyl)-L-valinate 5A. N-CBZ-monovalinate-monobenzyl-ganciclovir was prepared from monobenzyl ganciclovir by adding a solution of CBZ-L-valine-N-carboxy- anhydride (2.0 g) in dimethylformamide (0 ml) to a mixture of triethylamine (0.2 g), dimethylformamide (2 ml), and monobenzyl ganciclovir (2.0 g). The mixture was then diluted with more triethylamine (0.2 g), toluene (2.4 ml) and water (8 ml) and was vigorously stirred to initiate crystallization. More water (8 ml) was added and the mixture was cooled. The product was collected by filtration, washed with water and dried, to yield 3.1 g.

5B. Alternatively, N-CBZ-monovalinate-monobenzyl-ganciclovir was prepared from monobenzyl ganciclovir by adding a solution of CBZ-L-valine anhydride in dimethylformamide (50 ml) to a mixture of 4-dimethylamino-pyridine (3.8 g), dimethylformamide (50 ml), and monobenzyl ganciclovir (47.0 g). The anhydride was prepared by adding dicyclohexylcarbodiimide (36.0 g) to a stirred mixture of CBZ-L-valine (97.2 g) and ethyl acetate (280 ml). The mixture was stirred overnight, was filtered and the cake washed with ethyl acetate (150 ml). The filtrate was stripped and the residue dissolved in dimethylformamide and used as described above. Upon reaction completion, the mixture was diluted with triethylamine (20 g), toluene (50 ml) and water 200 ml) and was vigorously stirred to initiate crystallization. More water (200 ml) was added and the mixture was cooled. The product was collected by filtration, washed with water and dried, to yield 87.4 g.

5C. N-CBZ-monovalinate-monobenzyl-ganciclovir was prepared from monobenzyl ganciclovir hydrochloride as follows: To a mechanically stirred suspension of O-monobenzyl-ganciclovir HCl (25.0 g, 66.8 mmoles) in dimethylformamide (22 ml) at 4–7° C. under an atmosphere of nitrogen, was added triethylamine (7.4 g, 87 mmoles) at such a rate that the temperature of the slurry did not exceed 8° C. Once the addition was finished, the slurry was stirred at 4–6° C. while a solution of Z-Valine-NCA (24.0 g, 86 mmoles) in dimethyl-formamide (23 ml) was added dropwise. After the addition was finished, the ice bath was removed and the mixture was allowed to come to room temperature (23–25° C., approximately 30–45 min). Assay of the mixture by TLC (80:10:8 $CH_3CN:CH_3COOH:H_2O$) showed the reaction to be complete after this period of time. Successive addition to the mixture of triethylamine (2.2 g, 21.7 mmoles) toluene (17.5 ml) and water (20 ml) at 23–25° C. was followed by heating of the mixture to 40–46° C. The mixture was treated dropwise with additional water (80 ml) and then slowly cooled to 23–25° C. over a period of 2 hours. To the moderately vigorously stirred mixture was added water (100 ml) over a period of 10–15 minutes. The solid so formed was allowed to stir for a period of 10–15 minutes and then collected by filtration. The filtercake was washed with 2 portions of water (50 ml each) and air dried for 3 hours. Residual toluene was removed in vacuo at 35–40° C. Yield: 39.3 g (ca. 100%).

5D. N-CBZ-monovalinate-monobenzyl-ganciclovir can also be prepared advantageously in superior purity from monobenzyl ganciclovir hydrochloride as follows: CBZ-valine-NCA (1.15 equivalents) is dissolved in ethyl acetate and added to a slurry of monobenzyl ganciclovir (1.0 equivalent) in the presence of 4-dimethylaminopyridine (3% by weight) in dimethylformamide (DMF) and ethyl acetate at 23°–27° C. After the reaction mixture has been stirred for about 3 hours the mixture is analyzed by HPLC for progress of the reaction. Stirring of the reaction mixture is continued until the reaction is judged essentially complete. Water is added to quench the reaction and ethyl acetate is added to dilute the mixture. The organic phase is separated and the aqueous phase is again extracted with ethyl acetate. The combined ethyl acetate solution is washed twice with water, treated with activated carbon such as PWA carbon at 35°–40° C. and then filtered and azeotropically dried and concentrated to a premarked volume. Hexane is slowly added at 89° C. and the resulting mixture is slowly cooled to 25° C. to crystallize the product. The mother liquor is removed by decantation and the product is washed twice with an ethyl acetate/hexane (4/3) solution and once with hexane. The ethyl acetate/hexane and hexane washes are removed by decantation. The pure product is isolated by filtration and dried.

EXAMPLE 6

Preparation of 2-(2-amino-1,6-dihydro-6-oxo-purin-9-yl) methoxy-3-hydroxy-1-propyl-L-valinate hydrochloride Ganciclovir-L-valinate hydrochloride was prepared from N-CBZ-monovalinate-monobenzyl-ganciclovir as follows: A solution of the starting material (14.2 g) in methanol (100 ml) and conc. hydrochloric acid (2.7 g) was hydrogenated over palladium hydroxide on carbon (Pearlman's catalyst) (2.7 g). When the reaction was complete the mixture was filtered and the filtrate was concentrated under vacuum to a low volume. Water (9 ml) was added and the solution again stripped to remove residual methanol. Isopropanol (35 ml) was added and the mixture was stirred vigorously to initiate crystallization. More isopropanol (55 ml) was added and the mixture was stirred and cooled. The product was collected by filtration, washed with isopropanol and dried to yield 8.0 g; MS: 355 $(MH)^+$.

EXAMPLE 7

Preparation of 1-Benzyloxy-3-propionyloxy-2-(propionyloxy)methoxypropane, a compound of Formula (III)

7A. Preparation of Methoxymethyl propionate

To 710 ml of dimethoxymethane in a 3-liter 3-neck round bottom flask was added 14.0 g of Amberlyst 15. The mixture was heated to reflux and 950 ml of propionic anhydride was added as rapidly as possible (exothermic reaction) while the flask was cooled in an ice bath. The reaction temperature was allowed to rise to 50–55° C. The mixture was stirred for 5 minutes after the addition was complete and was then filtered directly onto 14.0 g of anhydrous potassium carbonate. The filtrate was fractionally distilled through an efficient column to separate residual dimethoxymethane, methyl propionate and the product (methoxymethyl propionate). Yield: 720.7 g (fraction 4); 83.6%; >99.5% pure.

7B. Preparation of 1-Benzyloxy-3-chloro-2-(propionyloxy) methoxypropane 204.0 g of 3-benzyloxy-1-chloro-2-propanol, 660 ml of hexane, 626.3 g of methoxymethyl propionate and 5.79 g of p-toluenesulfonic acid mono-hydrate were placed into a 2-liter 3-neck round bottom flask equipped with a thermometer, mechanical stirrer, nitrogen inlet and an efficient distillation column. The reaction mixture was heated to reflux. The distillate was taken off at about 10:1 to 15:1 reflux ratio keeping the head temperature below 60° C. Samples were taken to monitor the progress of the reaction. The reaction was quenched when the desired level of methyl acetal was reached which is usually less than about 4% methyl acetal. The quench was carried out by rapidly adding a solution of 11.55 g of sodium carbonate in 310 ml of water directly to the hot reaction mixture. The aqueous layer was washed with additional water and/or base to remove any residual propionic acid. The volatiles were removed to leave the crude product as a mobile liquid. Yield: 285.2 g, (97.8%); 92.6% pure.

7C. Preparation of 1-Benzyloxy-3-propionyloxy-2-(propionyloxy)methoxypropane 133.0 g of sodium propionate were placed into a 2-liter 3-neck round bottom flask equipped with a reflux condenser, nitrogen purge valve, thermometer and mechanical stirrer. 265.0 g of 1-benzyloxy-3-chloro-2-(propionyloxy) methoxypropane (from step a) and 700 ml of toluene were added, followed by a solution of 23.8 g of tetrabutylphosphonium chloride in 50 ml of toluene. The resulting suspension was vigorously stirred and heated to reflux for 16 hours. When GC assay of the reaction mixture showed completion of the reaction, the reaction mixture was cooled to 23° C. and 200 ml of 5% sodium carbonate solution was added. The mixture was stirred for 15 minutes to allow the salts to dissolve. The aqueous layer is then separated by decantation. The organic layer was washed twice with 300 ml of water and was then filtered through a plug (26.5 g) of adsorbent (silica-alumina [Davison Grade 135]). The solvent was removed under vacuum to give 298.2 g of product as a pale yellow oil. Yield: 99.4%; assay: 92.5%.

What is claimed is:

1. A process for preparing the compound 2-(2-amino-1,6-dihydro-6-oxo-purin-9-yl)methoxy-3-hydroxy-1-propyl-L-valinate or a pharmaceutically acceptable salt or diastereomers thereof, comprising:

(a) condensing a guanine derivative of Formula (II)

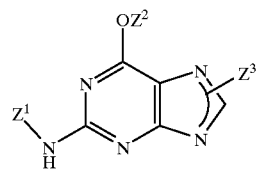

wherein the solid curved line between the two nitrogens of the imidazole ring together with $Z^3$ indicate a mixture of N-7 and N-9 isomers, $Z^1$, $Z^2$, and $Z^3$ are independently hydrogen or a silyl group of the formula —$SiR^5R^6R^7$, provided that at least one of $Z^1$, $Z^2$ and $Z^3$ must be a silyl group, in which $R^5$, $R^6$, and $R^7$ are independently lower alkyl, or optionally, $Z^1$ may be an amino-protecting group selected from the group consisting of acyl of the formula R—C(O)—, wherein R is alkyl of 1–6 carbon atoms; trityl, optionally substituted with methoxy, and N-(9-fluorenylmethoxycarbonyl, with a glycerol derivative of Formula (III)

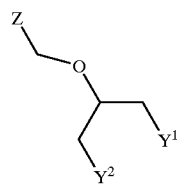

wherein $Y^1$ and $Y^2$ independently are aralkyloxy, or one of $Y^1$ and $Y^2$ is halo or acyloxy, wherein acyl is as defined above, and the other is aralkyloxy, and Z is a leaving group selected from acyloxy as defined above, benzoyloxy, halo, mesyloxy or tosyloxy, optionally in the presence of a catalyst, to produce a compound of Formula (IV)

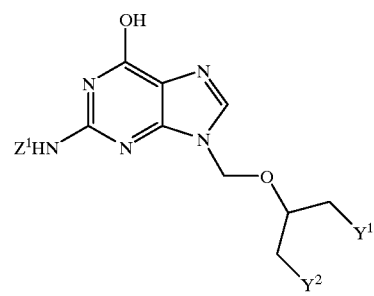

wherein $Z^1$ is hydrogen or an amino-protecting group as defined above, and $Y^1$ and $Y^2$ are as defined above;

(b) deprotecting the compound of Formula (IV) by basic hydrolysis when one of $Y^1$ and $Y^2$ is halo or acyloxy as defined above, and the other is aralkyloxy, or by hydrogenolysis when both $Y^1$ and $Y^2$ are aralkyloxy, to a compound of Formula (V)

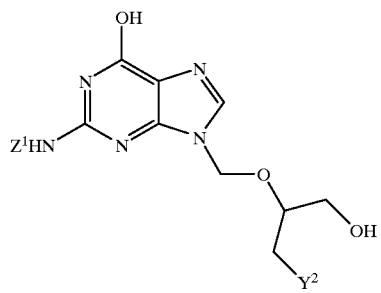

wherein $Z^1$ is as defined above, and $Y^2$ is aralkyloxy;

(c) optionally converting the compound of Formula (V) into an acid addition salt;

(d) esterifying the compound of Formula (V) with an activated protected derivative of L-valine of Formulae (VI) or (VIa)

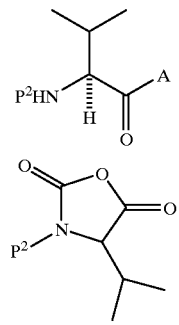

wherein A is a carboxy-activating group, and $P^2$ is an amino-protecting group, to produce a monovalinate of Formula (VII)

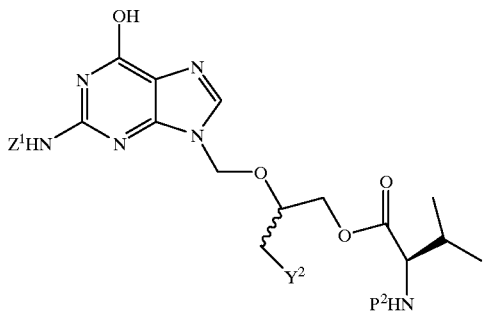

wherein $Z^1$ is as defined above, $P^2$ is an amino-protecting group and $Y^2$ is aralkyloxy; and (e) deprotecting the compound of Formula (VII) to 2-(2-amino-1,6-dihydro-6-oxo-purin-9-yl)methoxy-3-hydroxy-1-propyl-L-valinate or a pharmaceutically acceptable salt thereof; optionally followed by (f) converting 2-(2-amino-1,6-dihydro-6-oxo-purin-9-yl)methoxy-3-hydroxy-1-propyl-L-valinate into a pharmaceutically acceptable salt thereof; or (g) separating the 2-(2-amino-1,6-dihydro-6-oxo-purin-9-yl)methoxy-3-hydroxy-propyl-L-valinate into its (R) and (S) diastereomers.

2. The process of claim 1 wherein Z is lower acyloxy.

3. The process of claim 1 wherein the glycerol derivative is 1-benzyloxy-3-propionyloxy-2-propionyloxymethoxypropane, 1-benzyloxy-3-acetoxy-2-benzoyloxymethoxypropane or 1-benzyloxy-3-acetoxy-2-acetoxymethoxypropane.

4. The process of claim 1 wherein the catalyst of Step (a) is selected from a Lewis acid or perfluoroalkyl sulfonic acid.

5. The process of claim 4 wherein the catalyst is trifluoromethanesulfonic acid.

6. The process of claim 1 for preparing a compound of Formula (IV) wherein $Z^1$ is propionyl, $Y^1$ is benzyloxy and $Y^2$ is propionyloxy; or $Z^1$ is acetyl, $Y^1$ is benzyloxy and $Y^2$ is acetyloxy.

7. The process of claim 1 wherein the intermediate of Formula (V), in which $Z^1$ is hydrogen and $Y^2$ is aralkyloxy, is converted into the hydrochloride acid addition salt.

8. The process of claim 1 wherein the activated protected derivative of L-valine is a cyclic anhydride of Formula (VIa)

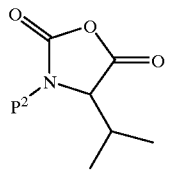

wherein $P^2$ is an amino protecting group.

9. The process of claim 8 wherein the activated protected derivative of L-valine is N-benzyloxycarbonyl-N-carboxy-L-valine anhydride.

10. The process of claim 1 wherein $P^2$ is benzyloxycarbonyl and Step (e) is done by hydrogenolysis.

11. The process of claim 10 wherein the hydrogenolysis is carried out in methanol/hydrochloric acid in the presence of palladium, palladium on carbon or palladium hydroxide on carbon.

12. The process of claim 11 in which the hydrogenolysis is carried out in the presence of palladium hydroxide on carbon.

13. The process for preparing a compound of Formula (IV)

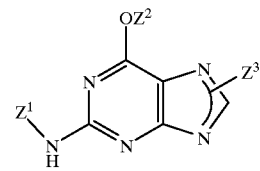

wherein $Z^1$ is acyl of the formula R—C(O)—, wherein R is alkyl of 1–6 carbon atoms; $Y^1$ is acyloxy, wherein acyl is as defined above; and $Y^2$ is aralkyloxy, comprising:

(a) condensing a guanine derivative of Formula (II)

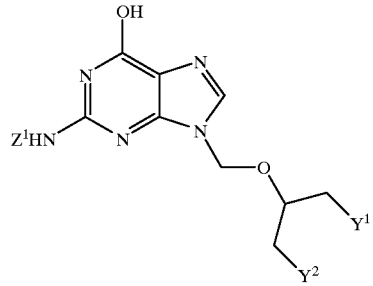

wherein the solid curved line between the two nitrogens of the imidazole ring together with $Z^3$ indicate a mixture of N-7 and N-9 isomers, $Z^1$, $Z^2$ and $Z^3$ are independently hydrogen or a silyl group of the formula —SiR$^5$R$^6$R$^7$, provided that at least one of $Z^1$, $Z^2$ and $Z^3$ must be a silyl group, in which $R^5$, $R^6$, and $R^7$ are independently lower alkyl, with a glycerol derivative of Formula (III)

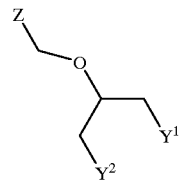

wherein $Y^1$ is acyloxy, wherein acyl is as defined above, $Y^2$ is aralkyloxy, and Z is a leaving group selected from acyloxy, wherein acyl is as defined above, benzoyloxy, halo, mesyloxy or tosyloxy, optionally in the presence of a catalyst selected from a Lewis acid or a perfluoroalkyl sulfonic acid; and (b) treating the product of step (a) with an acid anhydride of the formula (RCO)$_2$O, wherein R is alkyl of 1–6 carbon atoms.

14. The process of claim 13 wherein the catalyst is trifluoromethanesulfonic acid.

15. The process of claim 13 for preparing a compound of Formula (IV) wherein $Z^1$ is propionyl, $Y^1$ is propionyloxy and $Y^2$ is benzyloxy or $Z^1$ is acetyl, $Y^1$ is acetyloxy and $Y^2$ is benzyloxy.

16. A process for preparing a compound of Formula (V)

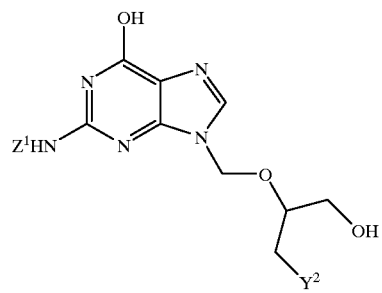

wherein $Z^1$ is hydrogen, and $Y^2$ is aralkyloxy, comprising:

deprotecting a compound of Formula (IV)

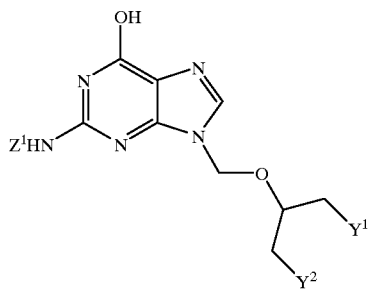

wherein $Z^1$ is acyl of the formula R—C(O)—, wherein R is alkyl of 1–6 carbon atoms; $Y^1$ is acyloxy, wherein acyl is as defined above; and $Y^2$ is aralkyloxy, by basic hydrolysis.

17. The process of claim 16 in which the intermediate of Formula (V) is converted into the hydrochloride acid addition salt.

* * * * *